(12) United States Patent
Shirai et al.

(10) Patent No.: US 11,051,695 B2
(45) Date of Patent: Jul. 6, 2021

(54) MAGNETIC RESONANCE IMAGING APPARATUS

(71) Applicant: Hitachi, Ltd., Tokyo (JP)

(72) Inventors: Toru Shirai, Tokyo (JP); Ryota Satoh, Tokyo (JP); Hisaaki Ochi, Tokyo (JP); Takenori Murase, Tokyo (JP); Yoshitaka Bito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/646,033

(22) PCT Filed: Jun. 1, 2018

(86) PCT No.: PCT/JP2018/021266
§ 371 (c)(1),
(2) Date: Mar. 10, 2020

(87) PCT Pub. No.: WO2019/049443
PCT Pub. Date: Mar. 14, 2019

(65) Prior Publication Data
US 2020/0260958 A1    Aug. 20, 2020

(30) Foreign Application Priority Data
Sep. 11, 2017 (JP) .............................. JP2017-174412

(51) Int. Cl.
*A61B 5/00*    (2006.01)
*A61B 5/055*   (2006.01)
(Continued)

(52) U.S. Cl.
CPC ............ *A61B 5/0042* (2013.01); *A61B 5/055* (2013.01); *G01R 33/4828* (2013.01); *G01R 33/543* (2013.01); *G01R 33/5608* (2013.01)

(58) Field of Classification Search
CPC .. A61B 5/0042; A61B 5/055; G01R 33/4828; G01R 33/543; G01R 33/5608; G01R 33/443; G01R 33/56
See application file for complete search history.

(56) References Cited

U.S. PATENT DOCUMENTS 5,539,316 A * 7/1996 Sukumar ............ G01R 33/3875
                                               324/318
9,448,289 B2    9/2016 Wang et al.
(Continued)

FOREIGN PATENT DOCUMENTS

JP     2017-184935 A    10/2017
WO    WO 2014/076808 A1    5/2014

OTHER PUBLICATIONS

International Search Report (PCT/ISA/210) issued in PCT Application No. PCT/JP2018/021266 dated Aug. 28, 2018 with English translation (four (4) pages).
(Continued)

*Primary Examiner* — Susan S Lee
(74) *Attorney, Agent, or Firm* — Crowell & Moring LLP (57) ABSTRACT

A magnetic resonance imaging apparatus includes: a static magnetic field generating magnet configured to generate a static magnetic field in a space where a subject is arranged; a transmission unit configured to transmit a high frequency magnetic field to the subject; a reception unit configured to receive a nuclear magnetic resonance signal generated in the subject due to transmission of the high-frequency magnetic field thereto; a gradient magnetic field application unit configured to apply a gradient magnetic field which adds positional information to the nuclear magnetic resonance signal; a computer configured to control the transmission unit, the reception unit, and the gradient magnetic field application unit, and configured to process the nuclear magnetic resonance signal; and a display unit configured to
(Continued)

display an image processed by the computer; and the computer performs a predetermined calculation processing.

6 Claims, 8 Drawing Sheets

(51) Int. Cl.
*G01R 33/48* (2006.01)
*G01R 33/54* (2006.01)
*G01R 33/56* (2006.01)

(56) References Cited

U.S. PATENT DOCUMENTS

2013/0221961 A1  8/2013 Liu
2015/0338492 A1  11/2015 Sato et al.
2019/0128991 A1  5/2019 Shirai et al.

OTHER PUBLICATIONS

Japanese-language Written Opinion (PCT/ISA/237) issued in PCT Application No. PCT/JP2018/021266 dated Aug. 28, 2018 (four (4) pages).

Schweser et al., "Quantitative Imaging of Intrinsic Magnetic Tissue Properties Using MRI Signal Phase: An Approach to in Vivo Brain Iron Metabolism?", NeuroImage, 2011, pp. 2789-2807, vol. 54, (19 pages).

Kim et al., "Robust Susceptibility Weighted Imaging Using Single-Slab 3D GRASE With Removal of Background Phase Variation", Proc. Intl. Soc. Mag. Reson. Med., 2013, pp. 2514, vol. 21, (one (1) pages).

Fang et al., "Background Field Removal Using a Region Adaptive Kernel for Quantitative Susceptibility Mapping of Human Brain", Journal of Magnetic Resonance, 2017, pp. 130-140, vol. 281 (12 pages).

* cited by examiner

MAGNETIC RESONANCE IMAGING APPARATUS

TECHNICAL FIELD

The present invention relates to a magnetic resonance imaging (MRI) technique. In particular, the present invention relates to an image processing technique for calculating a local phase distribution attributed to a difference between magnetic susceptibilities of biological tissues by use of a complex image taken with the Gradient Echo method.

BACKGROUND ART

A magnetic resonance imaging apparatus is a non-invasive tomography apparatus utilizing a nuclear magnetic resonance (NMR) in which a hydrogen nucleus (a proton) of a subject arranged in a static magnetic field resonates with a specific high frequency magnetic field. Since the NMR-signal generated in the subject changes according to various physical properties such as proton density, relaxing time, etc., the magnetic resonance imaging apparatus can visualize various biological information such as structure and composition of a biological tissue, cell property, etc., based on the NMR-signal.

In recent years, a magnetic susceptibility difference between biological tissues is attracting an attention as a measurable physical property with the magnetic imaging apparatus. The magnetic susceptibility is a physical property which indicates how largely a matter is magnetically polarized (magnetized) in a static magnetic field. Within a biological body, there exist a paramagnetic material such as deoxyhemoglobin and ferroprotein in a vein, and a diamagnetic material such as water, which occupies a major portion of a biological tissue, and calcium, a base for calcification. Since the magnetic resonance imaging apparatus can visualize the difference between the magnetic susceptibilities of the biological tissues, it is expected for possibility of applications to a diagnostic of cerebral ischemic condition, a prognosis for the effect of radiation treatment, a differential diagnosis of neurodegeneration condition, etc. As a method for visualizing the difference between the magnetic susceptibilities of the biological tissues, for example, Quantitative Susceptibility Mapping (QSM), Susceptibility Weighted Imaging (SWI), etc. are known.

The magnetic resonance imaging apparatus calculates a local phase distribution (a local distribution of phase variation) attributed to the difference between the magnetic susceptibilities of the biological tissues, and calculates a quantitative distribution of magnetic susceptibility from the local phase distribution using the QSM-method, or calculates a magnetic susceptibility image from the local phase distribution using the SWI-method. In the magnetic resonance imaging apparatus, when the local phase distribution is calculated, a total phase distribution is calculated by applying a phase wrapping correction, and a background phase elimination treatment for eliminating the background phase distribution generated due to a shape and the like of the subject from the total phase distribution is conducted. As representative methods for the background phase elimination treatment, the following two methods are so far proposed.

The first method is a method called as PDF (Projection onto Dipole Field)-method (for example, refer to the patent literature 1 (PTL1)). The PDF-method estimates a magnetic susceptibility of brain outside using a measured phase distribution in brain inside, calculates the phase distribution in the brain inside caused by the magnetic susceptibility distribution as a background phase distribution, and then calculates the local phase distribution by eliminating the background phase distribution from the total phase distribution, The second method is a method called as SHARP (Sophisticated Harmonic Artifact Reduction for Phase date)-method (refer for example to the non-patent literature 1 (NPTL1)). The SHARP-method utilizes the fact that the background phase distribution can be approximated by a spherical harmonic function. Namely, the background phase distribution and the local phase distribution are separated from the total phase distribution, utilizing the nature of a spherical mean value property that a value in any point is equal to an averaged value of points within a sphere (kernel) having any radius with a center at the any point.

CITATION LIST

Patent Literature

Patent Literature 1 (PTL1): U.S. Pat. No. 9,448,289B2

Non-Patent Literature

Non-Patent Literature 1 (NPTL1): Ferdinand Schweser et al., "Qunatitative imaging of intrinsic magnetic tissue properties using MRI signal phase; An approach to in vivo brain iron metabolism?", Nueroimage, 2011, Vol. 54, p. 2789-2807.

SUMMARY OF INVENTION

Technical Problem

However, the method described in PTL1 has a problem that the background phase distribution of a portion, for example paranasal cavity, etc. which cannot be reproduced by the estimated magnetic susceptibility of the brain outside, cannot be eliminated. Further, the method described in NPTL1 has a problem that the calculation accuracy is decreased for the local phase distribution in the interface portion between the brain inside and the brain outside (brain surface area).

The present invention is created for solving the above problem and aims at providing a magnetic resonance imaging apparatus by which the local phase distribution over the entire brain including the brain surface area.

Solution to Problem

In order to solve the above problem, a magnetic resonance imaging apparatus related to the present disclosure includes: a static magnetic field generation magnet configured to generate a static magnetic field in a space where a subject is arranged; a transmission unit configured to transmit a high frequency magnetic field to the subject; a reception unit configured to receive a nuclear magnetic resonance signal generated in the subject through transmission of the high frequency magnetic field thereto; a gradient magnetic field application unit configured to apply a gradient magnetic field which adds positional information to the nuclear magnetic resonance signal; a computer configured to control the transmission unit, the reception unit, and the gradient magnetic field application unit, and configured to process the nuclear magnetic resonance signal; and, a display unit configured to displaying an image processed by the computer; wherein the computer includes: a subject tissue extracting unit configured to compute an image of an extracted subject tissue, extracted as a subject tissue of the subject, from a complex image composed of the nuclear magnetic resonance signals, a phase distribution calculation unit configured to calculate the phase distribution from the complex image, a phase wrapping correction unit configured to correct a phase wrapping of the phase distribution, an area dividing unit configured to divide the phase distribution after correction into a predetermined area and an area other than the predetermined area of the subject tissue, based on the image of the extracted subject tissue, a background phase distribution calculation unit configured to calculate a background phase distribution of the predetermined area, and a local phase distribution calculation unit configured to calculate a local phase distribution in the predetermined area of the subject tissue by combination of the phase distribution after correction and the background phase distribution.

Advantageous Effect of the Invention

The present invention can provide a magnetic resonance imaging apparatus for accurately calculating a local phase distribution in the entire brain including the brain surface area.

DESCRIPTION OF EMBODIMENTS

An example of embodiment, to which the present invention is applied, will be explained. In the following, unless particularly explained, a same reference number is given to an object having a same function, and any repeated explanation will be omitted. Further, the present invention is not limited by the following explanation.

<<Entire Configuration of MRI-Apparatus>>

Figure 1A:
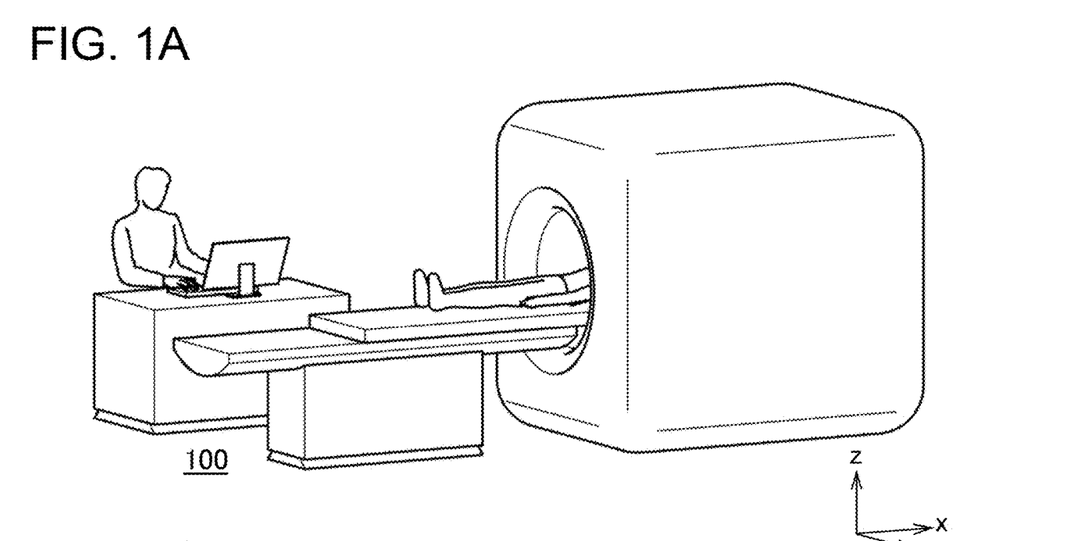
FIG. 1A shows an external view of a magnetic resonance imaging apparatus of a vertical magnetic field type related to the present embodiment.
Figure 1B:
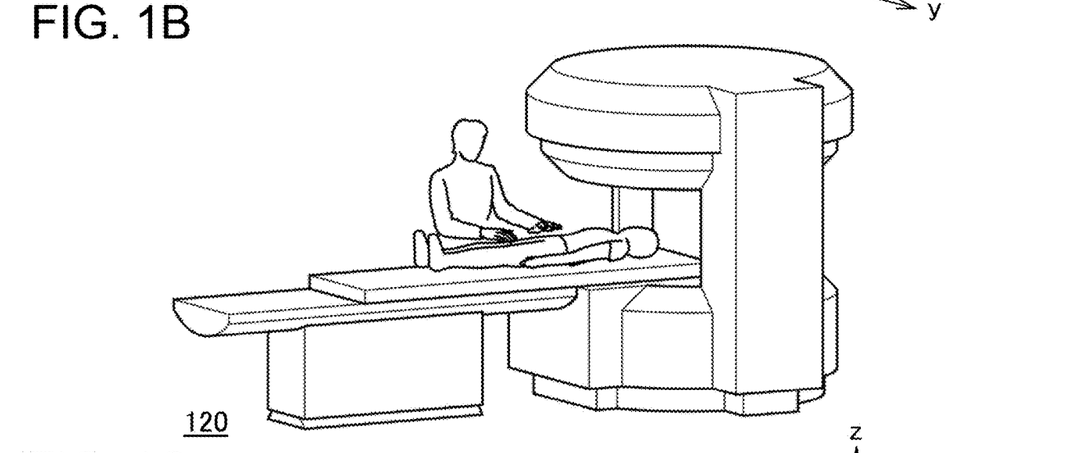
FIG. 1B shows an external view of a magnetic resonance imaging apparatus of a horizontal magnetic field type related to the present embodiment.
Figure 1C:
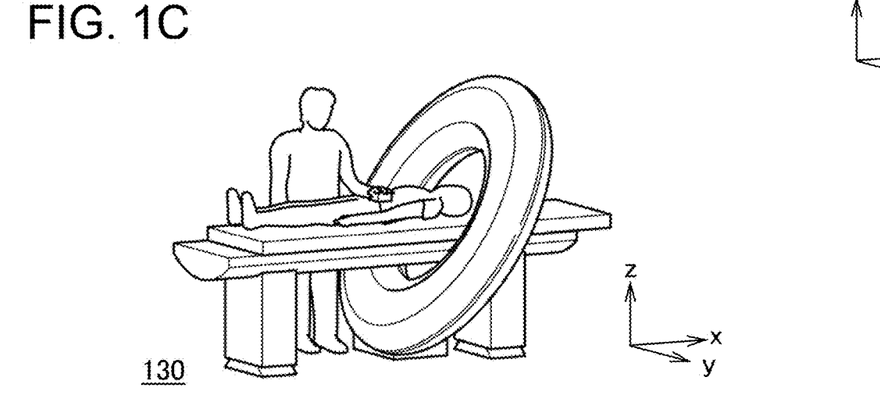
FIG. 1C shows an external view of a magnetic resonance imaging apparatus related to the present embodiment in which a sense of openness is enhanced.

FIG. 1 shows an external view of an MRI-apparatus related to the present embodiment. FIG. 1(a) shows an MRI-apparatus 100 of a horizontal magnetic field type utilizing a tunnel-type magnet for generating a static magnetic field with a solenoid coil. FIG. 1(b) shows an MRI-apparatus 120 of an open-type in which the magnet is separated into upper and lower ones for enhancing a sense of openness. Further, FIG. 1(c) shows an MRI-apparatus 130 utilizing a same tunnel-type magnet as FIG. 1(a) which, however, has a short depth and is arranged tilted for enhancing a sense of openness. It should be noted that the configuration of the MRI-apparatus in the present embodiment is not particularly limited, and therefore may have any of the forms shown in FIG. 1, and further may have any known configuration.

In the following, unless it is necessary to be particularly differentiated, an expression "MRI-apparatus 100" is used, representatively. In the MRI-apparatus 100, the static magnetic field direction of the MRI-apparatus 100 is z-direction, and one direction of two directions perpendicular to the z-direction, which is parallel to the bed surface where a subject 101 as a measurement object is arranged, is x-direction, and the other direction of the two directions is y-direction.

Figure 2:
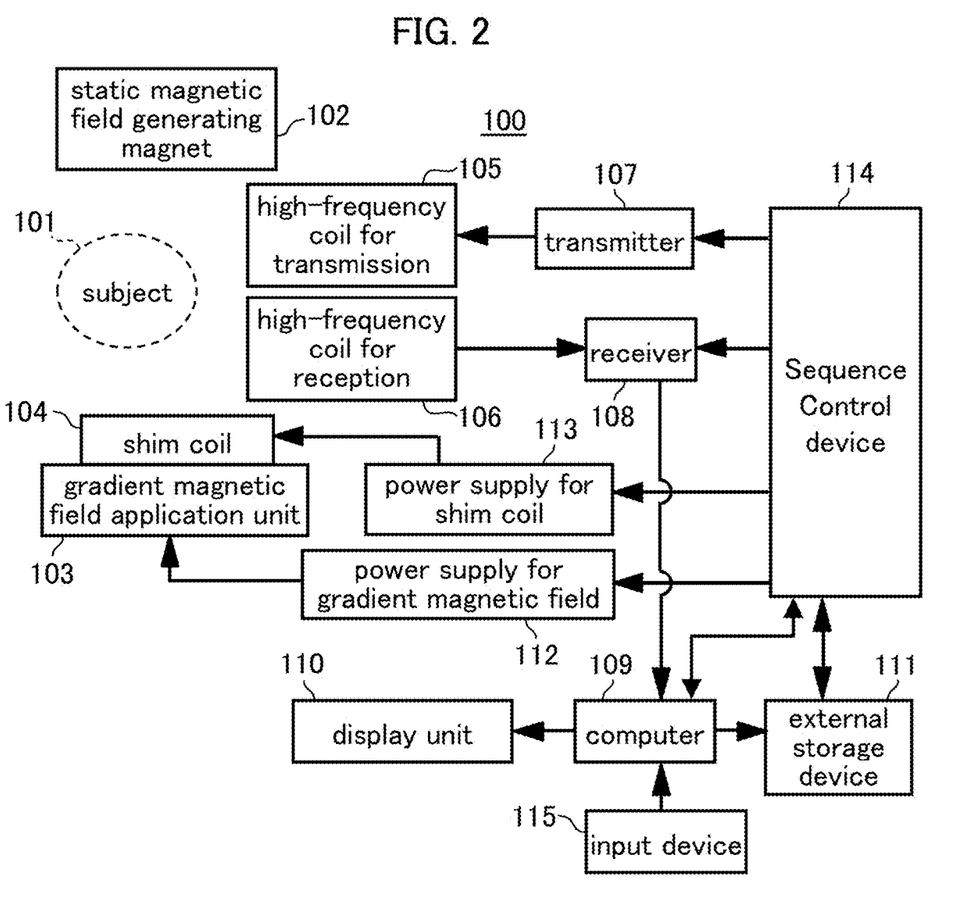
FIG. 2 shows schematically a block diagram of a magnetic resonance imaging apparatus related to the present embodiment.

FIG. 2 shows schematically a block diagram of a magnetic resonance imaging apparatus related to the present embodiment. As shown in FIG. 2, the MRI-apparatus 100 includes a static magnetic field generating magnet 102 which generates a static magnetic field in a space where a subject 101 is arranged, a high-frequency coil for transmission 105 which transmits a high-frequency magnetic field to the subject 101, a high-frequency coil for reception 106 which receives a nuclear magnetic signal generated in the subject 101 caused by the transmitted high-frequency magnetic field thereto, a gradient magnetic field application unit 103 which applies a gradient magnetic field which adds positional information to the nuclear magnetic resonance signal, a computer 109 which controls the transmission unit 105, the reception unit 106, and the gradient magnetic field application unit 103, as well as processes the nuclear magnetic resonance signal, and a display unit 110 which displays an image processed by the computer 109.

Further, the MRI-apparatus 100 includes a shim coil 104, a transmitter 107, a receiver 108, an external storage device 111, a power supply for gradient magnetic field 112, a power supply for the shim coil 113, a sequence control device 114, an input device 115, etc.

The static magnetic field generating magnet 102 generates a static magnetic field in a space where the subject 101 is arranged, for which a various form can be employed according to a configuration of the MRI-apparatus. The gradient magnetic field application unit 103 applies a gradient magnetic field in respective directions, x-, y-, and z-directions in a space where the subject 101 is arranged for adding information of spatial position to the nuclear magnetic resonance signal. The gradient magnetic fields applied to respective directions (x-direction gradient magnetic field, y-direction gradient magnetic field, z-direction gradient magnetic field) are, for example, phase-encode gradient magnetic field, read-out gradient magnetic field, and slice gradient magnetic field.

The shim coil 104 is a current coil used for adjusting the static magnetic field, such as for cancelling and removing non-uniformity of a static magnetic field generated in a space in which the subject 101 is arranged. The transmission unit 105 is a high-frequency coil for transmission, which transmits a high-frequency magnetic field to the subject 101 for excitation of hydrogen nuclei of the subject 101. The reception unit 106 is a high-frequency coil for reception, which receives a nuclear magnetic resonance signal generated in the subject 101 caused by the transmitted high-frequency magnetic field thereto. It should be noted that the transmission unit 105 and the reception unit 106 may be independently constructed units or may be one unit constructed for both purposes.

The transmitter 107 is controlled by the sequence controller 114 and generates a high-frequency magnetic field which is transmitted to the transmission unit 105. The receiver 108 is controlled by the sequence controller 114, detects a nuclear magnetic resonance signal received by the reception unit 106 and transmits a complex signal to the computer 109. It should be noted that the transmission unit 105 and the reception unit 106 may be independently constructed units or may be one unit constructed for both purposes.

The computer 109 is an information-processing equipment including a main memory, an auxiliary storage device, etc., to which a display unit 110, an external storage device 111, an input device 115, etc. are connected. The computer 109 controls the entire operation of the MRI-apparatus 100, reading out a control program stored in these storage devices, developing the control program in a working area, and executing this program, and performs various calculation. It should be noted that the computer 109 may be also a part of the MRI-apparatus 100, or an information-processing equipment independent from the MRI-apparatus 100, or an information-processing equipment which can transmit/receive data to/from the MRI-apparatus 100. Further, all or part of the functions which are achieved by the computer 109 may also be implemented as a hardware such as ASIC (Application Specific Integrated Circuit), FPGA (field-programmable gate array), etc.

The display unit 110 is, for example, configured with a liquid crystal display, an organic EL-display, etc. The display unit 110 displays the calculation results and various images on the display screen, based on the data acquired from the computer 109. The display unit 110 displays, for example, a local phase distribution, a quantitative distribution of magnetic susceptibility, an image of enhanced magnetic susceptibility, etc., on the display screen.

The external storage device 111, together with the auxiliary storage device, stores data used for various calculations performed by the computer 109, data generated in the course of calculations, data acquired by the various calculations, various conditions inputted via the input device 115, various parameters, etc.

The power supply for gradient magnetic field 112 is a power supply for driving the gradient magnetic field application unit 103, and controls driving of the gradient magnetic field application unit, based on a control instruction from the sequence controller 114. The power supply for the shim coil 113 is a power supply for driving the shim coil 104 and controls driving of the shim coil 104, based on a control instruction from the sequence control device 114.

The sequence control 114 controls the operations of respective units of the MRI-apparatus 100 such as the transmitter 107, the receiver 108, the power supply for gradient magnetic field 112, the power supply for shim coil 113, etc. For example, the sequence control device 114 controls an application timing of a high-frequency magnetic field, an application timing of a gradient magnetic field (x-direction gradient magnetic field, y-direction gradient magnetic field, z-direction gradient magnetic field), a reception timing of a nuclear magnetic resonance signal, etc., based on the settings information stored in the external storage device 111 or the auxiliary storage device (for example, based on a time chart called also as pulse sequence, which will be described later).

The input device 115 has a function for receiving an input operation by an operator and is configured, for example, with a keyboard, a camera, a mouse, a touch panel, a microphone for receiving a voice input, etc. The input device 115 is an interface for an operator to input various conditions, various parameters, etc. which are necessary for the computer 109 to perform various calculations and measurements. It should be noted that the various conditions, the various parameters, etc. can be set in advance, and that the operator can set these as appropriate via the input device 115.

<<Configuration of Computer>>

Figure 3:
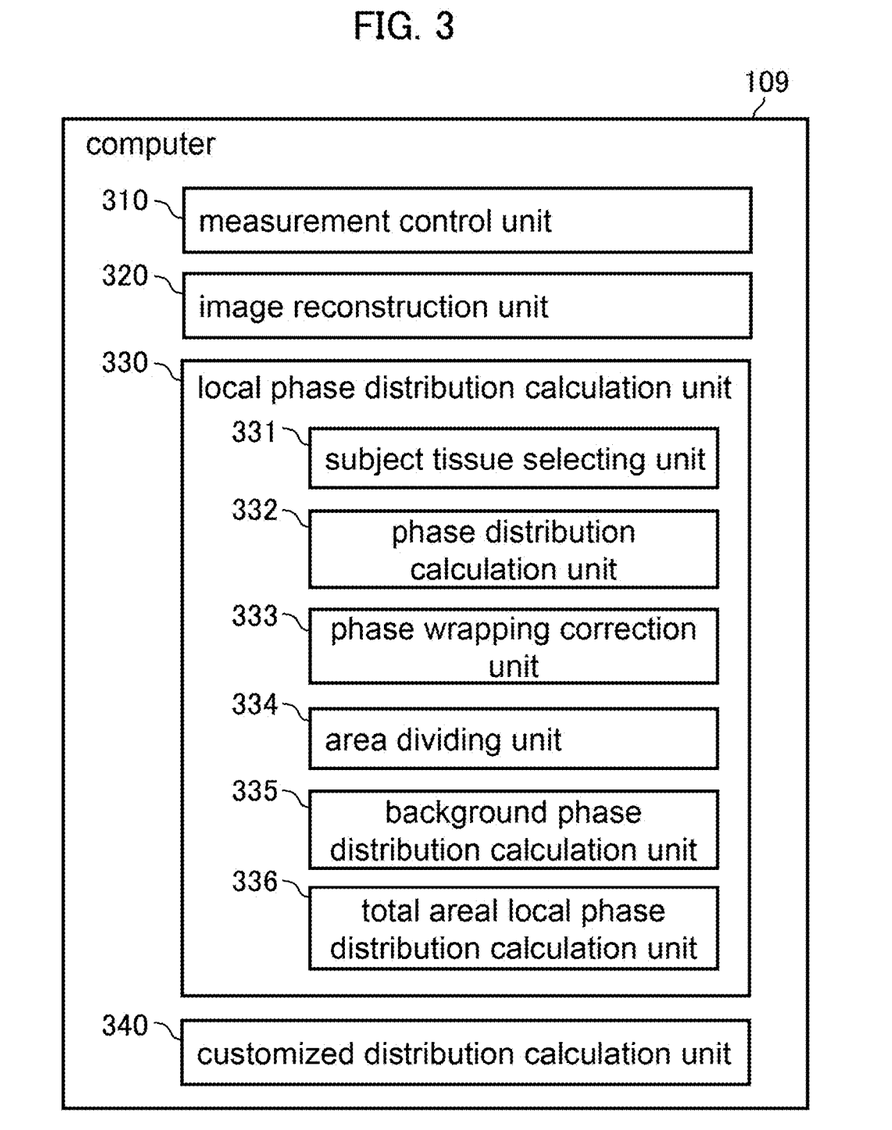
FIG. 3 shows a functional block diagram of a computer related to the present embodiment.

Next, in reference to FIG. 3, the configuration of the computer 109 related to the present embodiment is explained. In the present embodiment, an explanation is given for an example in which a brain of a subject 101 is used as a subject tissue.

Here, prior to the explanation about the configuration of the computer 109, an outline of a typical background phase removal process is explained.

First, the MRI-apparatus calculates a phase distribution P from a complex image taken by use of the Gradient Echo method with any echo time (a time duration from transmission of high-frequency magnetic field until reception of a nuclear magnetic resonance signal). Then, the MRI-apparatus performs a phase wrapping correction for correcting the wrapped phase occurring in the phase distribution P within the range $-\pi$ to $+\pi$.

The phase distribution after the phase wrapping correction (total phase distribution) $P_{total}$ is represented by use of the background phase distribution $P_{bkgr}$ caused by a shape of the subject tissue, the local phase distribution $P_{local}$ attributed to a difference between magnetic susceptibilities of biological tissues, as shown in eq. (1).

[eq.1]

$$P_{total}=P_{bkgr}+P_{local} \quad (1)$$

Further, the MRI-apparatus separates the background phase distribution $P_{bkgr}$ and the local phase distribution $P_{local}$ from the total phase distribution $P_{total}$, using the nature of an averaged value that a pixel-value in any pixel is approximately equivalent to an averaged pixel-value of pixels within a sphere (kernel) with a predetermined radius centered at the any pixel.

The background phase distribution satisfies the eq. (2), based on the nature of the averaged value.

[eq.2]

$$M_{shrink}((\delta-\beta_r)*P_{bkgr})=0 \quad (2)$$

where $\delta$ represents a delta function, $\rho_r$ a sphere kernel with radius r, and * a convolution integral. Further, $M_{shrink}$ represents a mask scaled down from a subject tissue extraction image M, which is an image of a subject tissue extracted from the subject 101, according to the radius r of the sphere kernel $\rho_r$.

The convolution integral A represented by eq. (2) can be transformed into eq. (3) by use of a Fourier transformation matrix F and a reversed Fourier transformation matrix $F^{-1}$.

[eq.3]

$$M_{shrink}F^{-1}CFP_{bker}=0 \quad (3)$$

where $C=F(\delta-\rho_r)$.

By substituting the eq. (1) into eq. (3), a relation of eq. (4) is obtained.

[eq.4]

$$M_{shrink}F^{-1}CFP_{local}=M_{shrink}F^{-1}CFP_{total} \quad (4)$$

Further, the MRI-apparatus calculates a local phase distribution $P_{local}$ satisfying the relation of eq. (4) from the total phase distribution $P_{total}$ and calculates a local phase distribution $P'_{local}$ represented by eq. (5) by use of least square method.

[eq. 5]

$$P'_{local} = \underset{P_{local}}{\operatorname{argmin}}\{\|M_{shrink}F^{-1}CF(P_{local} - P_{total})\|_2^2\} \quad (5)$$

Namely, in a typical background phase removal process using the SHARP method, only a local phase distribution in the range of the mask $M_{shrink}$ can be calculated, and therefore, there was a problem that calculation accuracy of a local phase distribution in an interface portion (brain surface area) between brain inside and brain outside decreases.

Thus, in the MRI-apparatus 100 related to the present embodiment, the total phase distribution is divided into the brain surface area and the brain inside area, and therefrom the local phase distribution in the entire brain including the brain surface area is calculated, combining the total phase distribution and the background phase distribution in the brain surface area. Herewith, an improvement of the calculation accuracy of the local phase distribution in the brain surface area becomes possible. In the following, the functional configuration of the computer 109 for achieving this improvement is explained.

The computer 109 includes a measurement control unit 310, an image reconstruction unit 320, a local phase distribution calculation unit 330, and a customized distribution calculation unit 340. Further, the local phase distribution calculation unit 330 includes a subject tissue extracting unit 331, a phase distribution calculation unit 332, a phase wrapping correction unit 333, an area dividing unit 334, a background phase distribution calculation unit 335, and a total areal local phase distribution calculation unit 336.

The measurement control unit 310, for example using the Gradient Echo method, transmits a high-frequency magnetic field from the transmission unit 105 to the subject 101, and thereby measures a nuclear magnetic resonance signal with any echo time generated in the subject 101 as a complex signal. The measurement control unit 310 controls the sequence control device 114 according to a predetermined pulse sequence and thereby controls the application timing of the high-frequency magnetic field, the application timing of the gradient magnetic field, the reception timing of the nuclear magnetic resonance signal, etc. It should be noted that the measurement control unit 310 may apply a flow compensation gradient magnetic field pulse in respective directions, x-, y-, z-directions, for compensating an influence from a flow such as a blood flow.

The image reconstruction unit 320 performs a Fourier transformation of a complex signal measured by the measurement control unit 310, arranging the complex signals in a 3-dimensional space k with coordinate-axes kr, kp, ks, and thereby a complex image, in which any pixel value is represented with a complex value, is reconstructed. When the space k is filled with nuclear magnetic resonance data, the image reconstruction unit 320 may use a method in which the nuclear magnetic resonance data are filled line by line in parallel to a coordinate axis of the space k (for example kr-axis), so-called Cartesian Filling Method, or may use a method in which the nuclear magnetic resonance data are filled radially with varying angles around the origin point of the space k, so-called Radial Scan Filling Method.

The local phase distribution calculation unit 330 calculates a local phase distribution in total area of the subject tissue, based on the complex image reconstructed by the image reconstruction unit 320. In particular, the subject tissue extracting unit 331 generates a subject tissue extraction image M in which a subject tissue of the subject 101 is extracted from a complex image. Then, the phase distribution calculation unit 332 calculates a phase distribution P from the complex image. Then, the phase wrapping correction unit 333 corrects the phase wrapping of the phase distribution P, and thereby calculates the total phase distribution $P_{total}$. Then, the area dividing unit 334 divides the total phase distribution $P_{total}$ into at least more than one area (for example, a predetermined area and an area other than the predetermined area), based on the subject tissue extraction image M. Then, the background phase distribution calculation unit 335 calculates a background phase distribution $P_{edge}$ in the predetermined area. Then, the total areal local phase distribution calculation unit 336 calculates the local phase distribution $P'_{local}$ in the total area of the subject tissue including the predetermined area, combining the total phase distribution $P_{total}$ and the background phase distribution $P_{edge}$ in the predetermined area.

The customized distribution calculation unit 340 calculates a customized distribution such as a quantitative magnetic susceptibility distribution, a magnetic susceptibility enhanced image, etc., by use of the local phase distribution $P'_{local}$ calculated by the local phase distribution calculation unit 330, and output the customized distribution to the display unit 110.

As explained above, the computer 109 related to the present embodiment extracts only the subject tissue from the complex image, divides the total phase distribution into a predetermined area and an area other than the predetermined area, calculates the background phase distribution in the predetermined area, and calculates the local phase distribution in the total area of the subject tissue. Due to this, the problem seen in the conventional SHARP method that errors become larger in the brain surface area corresponding to the radius of the kernel and the calculation accuracy of the local phase distribution in the brain surface area decreases can be prevented, and thereby the local phase distribution in the entire brain including the brain surface can be accurately calculated.

<<Flow of Calculation in the Computer>>

Figure 4:
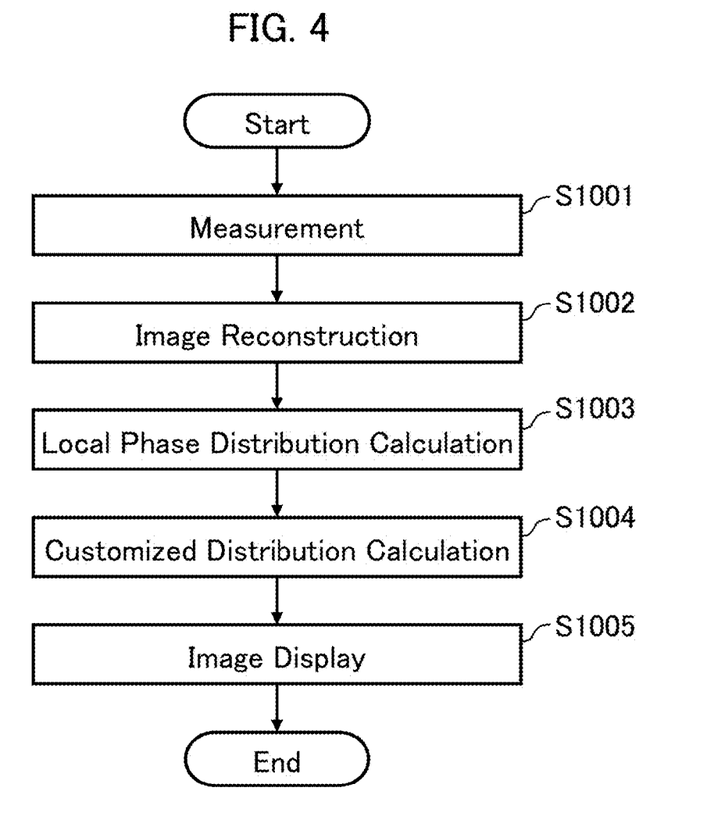
FIG. 4 shows a flow-chart for explaining a calculation flow in a computer related to the present embodiment.
Figure 5:
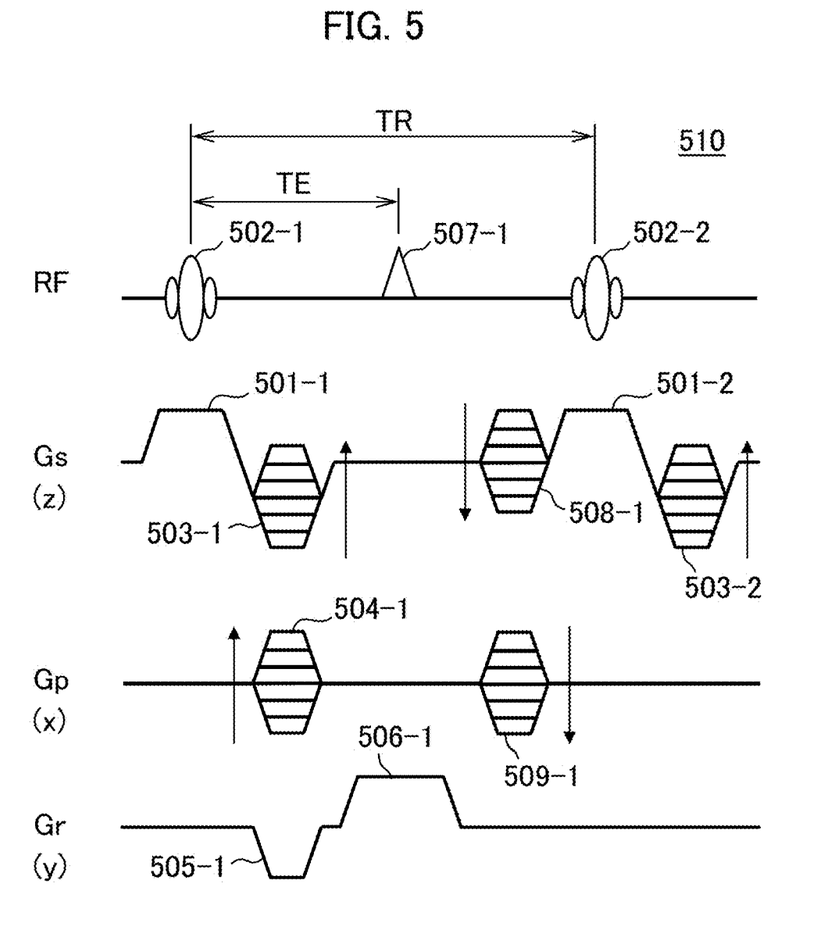
FIG. 5 shows a diagram for explaining a pulse sequence of RSSG (RF-spoiled-Steady-state Acquisition with Rewound Gradient-Echo)-sequence.
Figure 6:
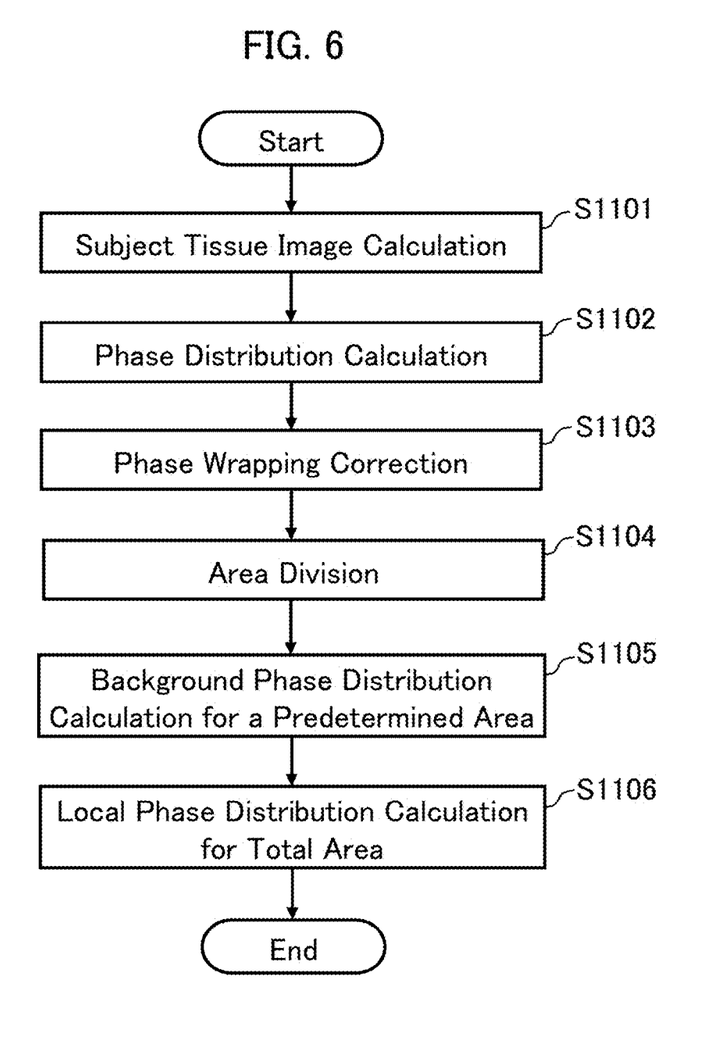
FIG. 6 shows a flow-chart for explaining a calculation flow of a local phase distribution in a local phase distribution calculation unit related to the present embodiment.
Figure 7A:
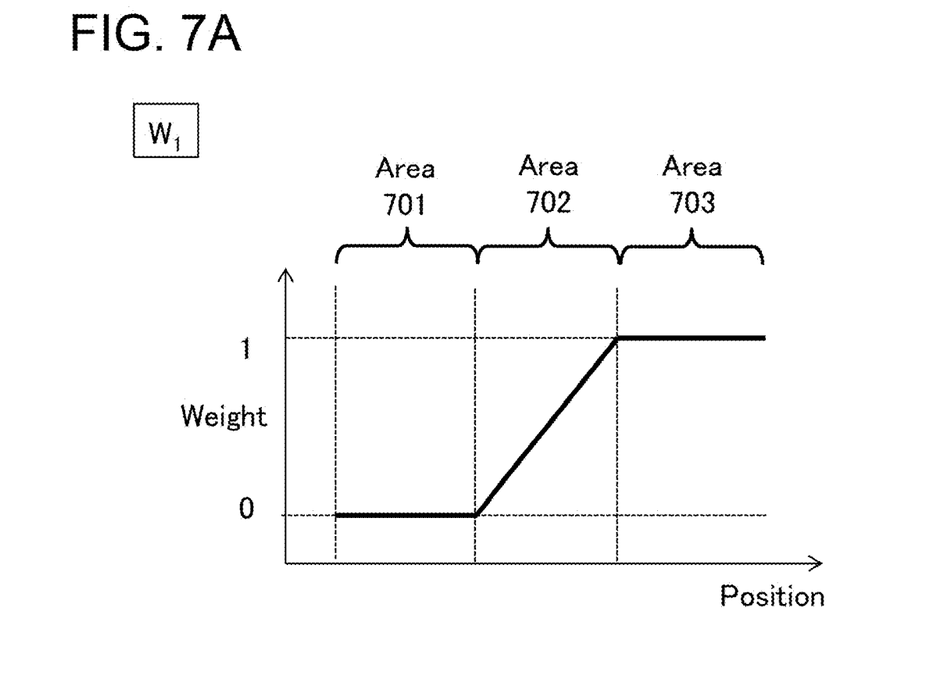
FIG. 7A shows a diagram for explaining a weighted image W1 which is used in a total-areal local phase distribution calculation unit related to the present embodiment.
Figure 7B:
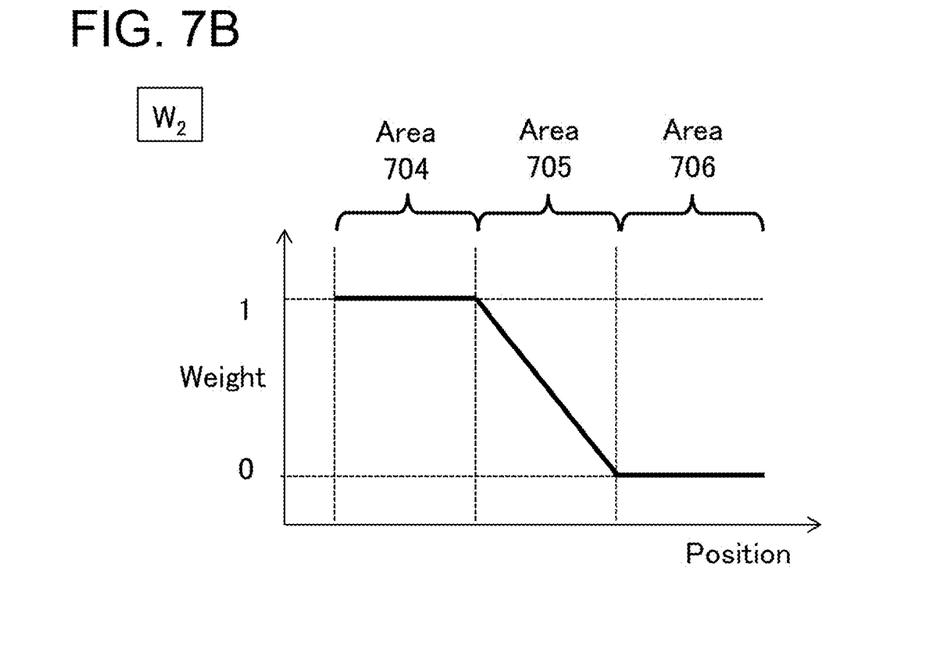
FIG. 7B shows a diagram for explaining a weighted image W2 which is used in a total-areal local phase distribution calculation unit related to the present embodiment.
Figure 8A:
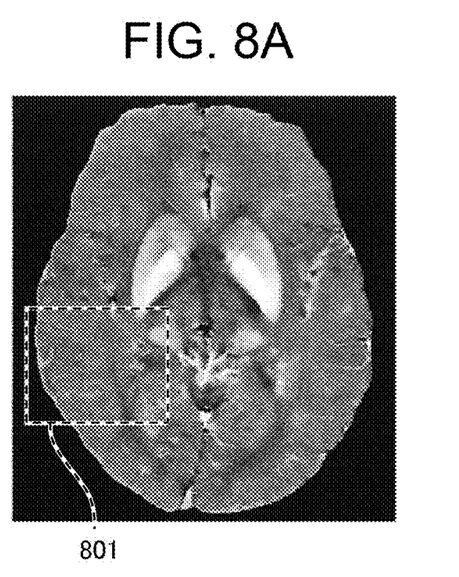
FIG. 8A shows an image which is processed with a computer related to the present embodiment.
Figure 8B:
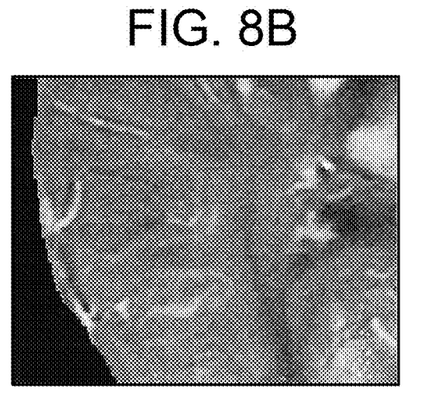
FIG. 8B shows an enlarged image of a portion of FIG. 8A.
Figure 8C:
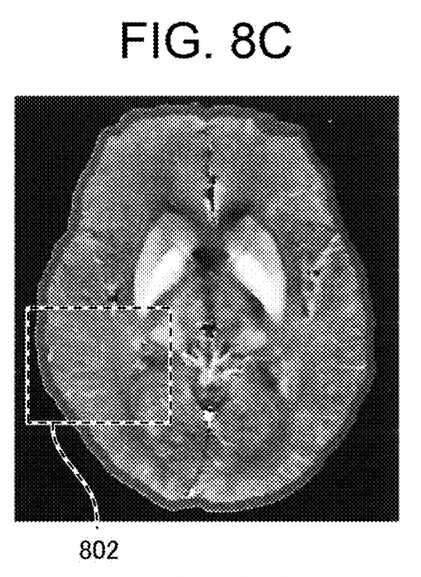
FIG. 8C shows an image which is processed with a conventional computer.
Figure 8D:
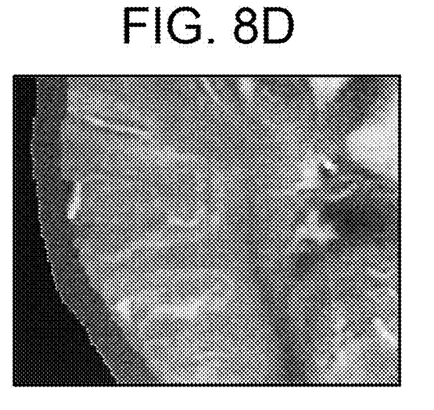
FIG. 8D shows an enlarged image of a portion of FIG. 8C.

Next, in reference to FIGS. 4 to 8, a calculation flow performed by the computer 109 related to the present embodiment is explained. FIG. 4 shows a flow-chart for explaining a calculation flow in the computer 109 related to the present embodiment. FIG. 5 shows a diagram for explaining a pulse sequence of RSSG-sequence. FIG. 6 shows a flow-chart for explaining a calculation flow of a local phase distribution in a local phase distribution calculation unit 330 related to the present embodiment. FIG. 7 shows a diagram for explaining a weighted image which is used in the total-areal local phase distribution calculation unit 336 related to the present embodiment. FIG. 8 shows examples of images displayed in the display unit 110 related to the present embodiment.

[Measurement: S1001]

In step S1001, the computer 109 performs measurement processing.

An operator sets various parameters (for example, number of nuclear magnetic resonance signals, echo time, time interval of echo time, etc.) via the input device 115, then, when an imaging start instruction is inputted to the computer 109, the measurement control unit 310 controls the sequence control device 114 according to the predetermined pulse sequence. Then the measurement control unit 310 measures a nuclear magnetic resonance signal with any echo time as a complex signal.

Here, in reference to FIG. 5, a pulse sequence of a type of the Gradient Echo method, which is used by the measurement control unit for measurement, is explained. The RSSG sequence 510 (RSSG: RF-spoiled-Steady-state Acquisition with Rewound Gradient-Echo) is a pulse sequence which is sensitive to a local magnetic field change resulting from a magnetic susceptibility difference between the biological tissues. It should be noted that the sequence used by the measurement control unit 310 for measurements is not limited to the RSSG sequence 510.

In FIG. 5, RF represents a high-frequency magnetic field, Gs a slice gradient magnetic field, Gp a phase-encode gradient magnetic field, and Gr a read-out gradient magnetic field. Further, TE represents an echo time, and TR a repetition period. Furthermore, 501 represent a slice gradient magnetic field pulse, 502 a high-frequency magnetic field pulse, 503, 508 slice-encode gradient magnetic field pulses, 504, 509 phase-encode gradient magnetic field pulses, 505, 506 read-out gradient magnetic field pulses, and 507 a nuclear magnetic resonance signal. It should be noted that a number after a hyphen indicates how many times the measurements are already repeated by the measurement control unit 310, and, for example, "−2" indicates that the measurement repeated by the measurement control unit 310 is a second one.

The measurement control unit 310 controls the sequence control device 114 according to the RSSG sequence 510 and measures data necessary for image reconstruction, thereby appropriately controlling application timings of the slice gradient magnetic field pulse 501, the high-frequency magnetic field pulse 502, the slice-encode gradient magnetic field 503, the phase-encode gradient magnetic field pulse 504, the read-out gradient magnetic field pulse 505, the read-out gradient magnetic field pulse 506, the slice-encode gradient magnetic field pulse 508, the phase-encode gradient magnetic field pulse 509, etc.

In the RSSG sequence 510 shown in FIG. 5, one nuclear magnetic resonance signal 507 is measured within a repetition period TR.

First, when a subject 101 is arranged in a static magnetic field, since a hydrogen nucleus in the subject 101 takes on a specific frequency corresponding to the static magnetic field strength, the transmission unit 105 transmits a high-frequency magnetic field pulse 502-1 having a frequency in agreement with the specific frequency of the hydrogen nucleus to a measurement area of the subject 101, thereby exciting the hydrogen nucleus of the subject 101. Here, the gradient magnetic field application unit 103 applies a slice gradient magnetic field pulse 501-1 to the measurement area of the subject 101 in z-direction, and thereby selectively excites magnetization of a predetermined slice (imaging position of a 3-dimensional image) in the subject 101.

It should be noted that, when repeated measurements are performed, the measurement control unit 310 changes the phase of the high-frequency magnetic field 502 by a predetermined angle (for example 117°, 122°). For example, the predetermined angle is 117° for the first measurement of the repeated measurements, then for the second measurement of the repeating measurements the angle is 117°×2, and then for the third measurement of the repeating measurements the angle is 117°×3. Due to this, in the next application of the high-frequency magnetic field, a measurement can be conducted appropriately without an unnecessary residual signal component.

Subsequently, the gradient magnetic field application unit 103 applies a slice-encode gradient magnetic field pulse 503-1 to the measurement area of the subject 101 in z-direction, thereby adding a positional information of the slice-encode direction to the magnetization phase in a magnetization phase. Further, the gradient magnetic field application unit 103 applies a phase-encode gradient magnetic field pulse 504-1 to the measurement area of the subject 101 in x-direction, thereby adding a positional information of the phase-encode direction to the magnetization phase. Namely, the gradient magnetic field application unit 103 adds positional information to the magnetization phases in z- and x-directions, in advance to read-out of the nuclear magnetic resonance signal.

The slice-encode gradient magnetic field pulse 503-1 changes its magnetic field strength for every repetition periods TR. For example, the seven horizontal lines shown in FIG. 5 indicate different strengths of the gradient magnetic field and indicate a stronger positive gradient magnetic field as it goes upwards along an upward arrow. Similarly, also the phase-encode gradient magnetic field pulse 504-1 changes its magnetic field strength for every repetition periods TR. For example, the seven horizontal lines shown in FIG. 5 indicate different strengths of the gradient magnetic field and indicate a stronger positive gradient magnetic field as it goes upwards along an upward arrow.

Though, in reference to FIG. 5, it has been explained exemplarily that the slice-encode gradient magnetic field 503-1 and the phase-encode gradient magnetic field 504-1 change their magnetic field strengths in seven ways, it should be noted that the present invention is not limited to this example.

Subsequently, the gradient magnetic field application unit 103 applies the read-out gradient magnetic field 505-1 for dephasing to the measurement area of the subject 101 in y-direction and diffuses the phases of magnetizations within pixels. Further, the gradient magnetic field application unit 103 applies the read-out gradient magnetic field 506-1 to the measurement area of the subject 101 in y-direction, thereby adding a positional information of the read-out direction to the magnetization phase. This makes it possible that the measurement control unit 310 measures one nuclear magnetic resonance signal 507 within a repetition period TR.

At last, the gradient magnetic field application unit 103 applies the slice-encode gradient magnetic field 508-1 for rephasing to the measurement area of the subject 101 in z-direction, and, further, applies the slice-encode gradient magnetic field 509-1 for rephasing to the measurement area of the subject 101 in x-direction, thereby converging the dephased magnetization phases within pixels.

The slice-encode gradient magnetic field pulse 508-1 changes its magnetic field strength for every repetition period TR. For example, the seven horizontal lines shown in FIG. 5 indicate different strengths of the gradient magnetic field and indicate a stronger negative gradient magnetic field as it goes downwards along a downward arrow. Similarly, also the phase-encode gradient magnetic field pulse 509-1 changes its magnetic field strength for every repetition periods TR. For example, the seven horizontal lines shown in FIG. 5 indicate different strengths of the gradient magnetic field and indicate a stronger negative gradient magnetic field as it goes downwards along a downward arrow.

The measurement control unit 310 repeats the above procedure with varying the phase of the high-frequency magnetic field pulse 502, the strengths of the slice-encode gradient magnetic field pulses 503, 508, and the strengths of the phase-encode gradient magnetic field pulses 504, 509, and thereby measures the nuclear magnetic resonance signal 507 necessary for image reconstruction. It should be noted that, when the echo time is set to be shorter, the absolute values of pixels of a complex image obtained with the RSSG-sequence 510 turn to be a T1(a vertical relaxation time)-enhanced image, and, when the echo time is set to be longer, they turn to be a T2*(an apparent horizontal relaxation time)-enhanced image which reflects the diffusing of phases within pixels. In the present embodiment, the echo time TE is set to be longer and thus the T2*enhanced image is taken.

[Image Reconstruction: S1002]

In step S1002, the computer 109 performs an image reconstruction processing.

The image reconstruction unit 320 reconstructs a complex image by arranging the nuclear magnetic resonance signals, which have been measured in step S1001, in the k-space and performing a Fourier-transformation thereof. For the imaging method, there is no special limitation and a known method such as the cartesian imaging, non-cartesian imaging, multi-echo planner imaging method, etc. can be applied.

[Local Phase Distribution Calculation: S1003]

In step S1003, the computer 109 performs the local phase distribution calculation processing.

Here, in reference to FIG. 6, a flow of the local phase distribution calculation is explained in detail. The local phase distribution calculation unit 330 calculates the local phase distribution in total area of the subject tissue, based on the complex image reconstructed in step S1002.

In step S1101, the subject tissue extracting unit 331 calculates a subject tissue extraction image M, in which a subject tissue of the subject 101 is extracted, based on the magnitudes of the absolute values of pixels (absolute-value image) in the complex image reconstructed by the image reconstruction unit 320. The subject tissue extracting unit 331 separates a noise component and a signal component from a histogram of the pixel-values of the absolute-value image by use of, for example, a known method such as discriminant analysis method, and then calculates the subject tissue extraction image M in which a subject tissue of the subject 101 is extracted (for example an image in which the pixel-values of brain inside are set to 1 and the pixel-values of brain outside are set to 0). It should be noted that the subject tissue extracting unit 331 may remove unnecessary areas (for example areas such as subcutaneous fat) by use of, for example, a known method such as Region Growing method, and thereby may calculate the subject tissue extraction image M in which only the substantial area of the subject tissue necessary for calculation of the magnetic susceptibility is extracted by eliminating areas, for example such areas as subcutaneous fat which is unnecessary for calculation of magnetic susceptibility distribution, from the complex image.

In step S1102, the phase distribution calculation unit 332 calculates the phase distribution P, based on argument components of the reconstructed complex image reconstructed by the image reconstruction unit 320.

In step S1103, the phase wrapping correction unit 333 calculates the total phase distribution $P_{total}$, correcting the phase wrapped in a range of $-\pi$ to $+\pi$, which is a result in the phase distribution P calculated in step S1102, for example, by use of a known method such as the Region Growing method.

In step S1104, the area dividing unit 334 divides the total phase distribution $P_{total}$ into at least 2 areas or more, namely into a predetermined area of the subject tissue and an area other than the predetermined area of the subject tissue, based on the subject tissue extraction image M calculated in step S1101. The predetermined area of the subject tissue represents, for example, a brain surface area which is an interface portion between an area of pixel-values 1 and an area of pixel-values 0, where 1 stands for a pixel-value of brain inside and 0 stands for a pixel-value of brain outside. Further, the area other than the predetermined area of the subject tissue represents, for example, the area of brain inside excluding the brain surface area. It should be noted that the area defined as the brain surface area is determined by the radius r of a sphere kernel $\rho_r$ (kernel size) which is used by the total areal local phase distribution calculation unit 336 for calculation of the local phase distribution in the total area of the subject tissue, as explained later in step S1106.

In step S1105, the background phase distribution calculation unit 335 calculates the background phase distribution $P_{edge}$ in the predetermined area of the subject tissue (for example, the brain surface area) from the total phase distribution $P_{total}$ calculated in step S1103. In the following, the calculation method for the background phase distribution $P_{edge}$ in the predetermined area of the subject tissue is explained.

The background phase distribution calculation unit 335 calculates the background phase distribution $P_{edge}$ in the predetermined area of the subject tissue from the total phase distribution $P_{total}$, by use of a local polynomial approximation.

The background phase distribution calculation unit 335 calculates the polynomial coefficients $A_{k,l,n}$ satisfying the eq. (6), assuming the position of any pixel in the local area to be (x, y, z).

[eq. 6]

$$A'_{k,l,n} = \underset{A_{k,l,n}}{\operatorname{argmin}} \left\{ \left\| M\left( P_{total}(x,y,z) - \sum_{n=0}^{N}\sum_{l=0}^{L}\sum_{k=0}^{K} A_{k,l,n} x^k y^l z^n \right) \right\|_2^2 \right\} \quad (6)$$

where K stands for the order of the polynomial in x-direction, L for the order of the polynomial in y-direction, and N for the order of the polynomial in z-direction, respectively.

Assuming the position of the center pixel in the local area to be $(x_0, y_0, z_0)$, the background phase distribution $P_{edge}$ in the predetermined area of the subject tissue can be calculated by eq. (7).

[eq. 7]

$$P_{edge}(x_0,y_0,z_0) = A_{0,0,0} \quad (7)$$

The background phase distribution calculation unit 335 calculates the background phase distribution $P_{edge}$ by applying the eq. (7) to all pixels in the predetermined area of the subject tissue.

In step S1106, the total areal local phase distribution calculation unit 336 calculates the local phase distribution $P'_{local}$ in the total area of the subject tissue, combining the total phase distribution $P_{total}$ and the background phase distribution $P_{edge}$ in the predetermined area of the subject tissue. In the following, calculation method of the local phase distribution $P'_{local}$ in the total area of the subject tissue is explained.

The total areal local phase distribution calculation unit 336 calculates an estimated value for the local phase distribution $P'_{local}$ in the total area of the subject tissue, by use of constrained least squares method.

[eq. 8]

$$P'_{local} = \underset{P_{local}}{\mathrm{argmin}}\{\|W_1 F^{-1} CF(P_{local} - P_{total})\|_2^2 + \|W_2(P_{edge} - (P_{local} - P_{total}))\|_2^2\} \quad (8)$$

where $W_1$ represents an image with smaller weight in the brain surface area, and $W_2$ represents an image with larger weight in the brain surface area.

The first term in eq. (8) represents, similarly to the SHARP method, a constrained term based on the nature of average value in the area of brain inside. For the constrained term satisfying the condition in the nature of average value, the weight in the area of brain inside is set larger and the weight in the brain surface area is set smaller.

The second term in eq. (8) represents the constrained term based on the background phase distribution in the brain surface area. For the constrained term based on the background phase distribution in the brain surface area, the weight in the brain surface area is set larger and the weight in the area of brain inside is set smaller.

Here, in reference to FIG. 7, the relation between the weighted images $W_1$, $W_2$ and the eq. (8) is explained. FIG. 7(a) shows a one-dimensional profile of the weighted image $W_1$. FIG. 7(b) shows a one-dimensional profile of the weighted image $W_2$. The horizontal axis represents a position, and the vertical axis represents a weight.

In FIG. 7, the combined area of the area 701 and the area 702 represents the brain surface area, and the area 703 represents the area of brain inside excluding the brain surface area (area other than the brain surface area). Similarly, the combined area of the area 704 and the area 705 represents the brain surface area, and the area 706 represents the area of brain inside excluding the brain surface area (area other than the brain surface area). It should be noted that the area 701 (area 704) and the area 702 (area 705) are set to be larger than the radius r of a sphere kernel $\rho_r$.

As shown in FIG. 7, the total areal local phase distribution calculation unit 336 sets the weight in the area 701 to be 0, the weight in the area 703 to be 1, and the weight in the transitional area 702 from the area 701 to the area 703 to be a value from 0 to 1 (a linearly varying value). Further, the total areal local phase distribution calculation unit 336 sets the weight in the area 704 to be 1, the weight in the area 706 to be 0, and the weight in the transitional area 705 from the area 704 to the area 706 to be a value from 1 to 0 (a linearly varying value).

Namely, using the weighted images W1 and W2, the total areal local phase distribution calculation unit 336 increases the weight in the area of brain inside and decreases the weight in the brain surface area so that the constrained terms based on the nature of average value shown in eq. (8) can be calculated with an equivalent accuracy as the SHARP method (refer to eq. (5)).

Further, using the weighted images W1 and W2, the total areal local phase distribution calculation unit 336 increases the weight in the brain surface area and decreases the weight in the area of brain inside so that the constrained terms based on the background phase distribution in the brain surface area shown in eq. (8) can be made closer to the background phase distribution in the brain surface area calculated with the local polynomial approximation.

Further, using the weighted images $W_1$ and $W_2$, the total areal local phase distribution calculation unit 336 varies the weights linearly between 0 and 1 in the areas 702 and 703 so that the brain surface area (the combined area of the areas 701 and 702, the combined area of the areas 704 and 705) and the area of brain inside (the areas 703, 706) can be smoothly joined.

It should be noted that the total areal local phase distribution calculation unit 336 may also calculate the local phase distribution in the total area of the subject tissue (total brain including the brain surface area) not only by use of the constrained least square as shown in eq. (8), but also by use of the regularized least square method (using a condition to minimize the regularization term of the local phase distribution) as shown in eq. (9).

For example, the total areal local phase distribution calculation unit 336 can also calculate the local phase distribution in the total area of the subject tissue, applying eq. (9) in which a regularization term taking into account the deviation of the pixel-values in the local phase distribution $P_{local}$ is inserted.

[eq. 9]

$$P'_{local} = \underset{P_{local}}{\mathrm{argmin}}\{\|W_1 F^{-1} CF(P_{local} - P_{total})\|_2^2 + \lambda_1\|W_2(P_{edge} - (P_{local} - P_{total}))\|_2^2 + \lambda_2\|P_{local}\|_2^2\} \quad (9)$$

where $\lambda_1$ is a regularization parameter for adjusting the constraint degree in the predetermined area of the subject tissue. $\lambda_2$ is a regularization parameter for allowing the deviation of the local phase distribution $P_{local}$ to some extent.

The first term in eq. (9) represents, similarly to the SHARP method, a constraint term based on the nature of average value in the area of brain inside.

The second term in eq. (9) represents a constraint term based on the background phase distribution in the brain surface area.

The third term in eq. (9) represents a regularization term having a role to prevent an excessive removal of the local phase variation component from the phase distribution.

According to the calculation procedure with the computer 109 related to the present embodiment, using eq. (8) and eq. (9), it has been demonstrated that the calculation accuracy of the local phase distribution in the area of brain inside can be largely improved in comparison to a conventional method, while keeping an approximately equivalent calculation accuracy to the conventional SHARP method. Namely, according to the calculation procedure of the computer 109 related to the present embodiment, it has been demonstrated that the local phase distribution of the total brain including the brain surface area can be calculated with high accuracy, using the constraint term based on the nature of average value in the area of brain inside and the constraint parameter based on the background phase distribution in the brain surface area.

[Customized Distribution Calculation: S1004]

In step S1004, the computer 109 conducts the customized distribution calculation.

The customized distribution calculation unit 340 calculates a customized distribution such as a quantitative magnetic susceptibility distribution, a magnetic susceptibility enhanced image, etc., by use of the local phase distribution $P'_{local}$ and by use of the QSM method or the SWI method. For example, the customized distribution calculation unit 340 includes a local magnetic field calculation unit and a magnetic susceptibility calculation unit and calculates a quantitative magnetic susceptibility distribution by use of the QSM method. Further, for example, the customized distribution calculation unit 340 includes a mask generation unit and a magnetic susceptibility enhancing unit and calculates the magnetic susceptibility enhanced image by use of the SWI method. In the following, as a specific example of processing performed by the customized distribution calculation unit 340, a calculation method for the quantitative magnetic susceptibility distribution by use of the QSM method and a calculation method for the magnetic susceptibility enhanced image by use of the SWI method are explained.

[Calculation Method for Quantitative Magnetic Susceptibility Distribution by Use of QSM Method]

First, the calculation method for the quantitative magnetic susceptibility distribution by use of the QSM method is explained. The QSM method utilizes the fact that a local phase distribution $P_{local}$ reflects a magnetic susceptibility difference between the biological tissues, calculates a local magnetic field distribution from a local phase distribution $P_{local}$, and further calculates a quantitative magnetic susceptibility distribution by use of a relation between magnetic field and magnetic susceptibility.

Assuming the position vector r, a relative magnetic field distribution attributed to a magnetic susceptibility difference between the biological tissues is represented by eq. (10).

[eq. 10]

$$\delta(r) = -\frac{2\pi P_{local}(r)TE}{\gamma \cdot B_0} \quad (10)$$

where $\gamma$ is the nuclear gyromagnetic ratio of a proton, $B_0$ is a static magnetic field strength.

Here, the local magnetic field distribution is represented by eq. (11) derived from the Maxwell equation for static magnetic field.

[eq. 11]

$$\delta(r) = \frac{1}{4\pi} \int \chi(r') \frac{3\cos^2\alpha - 1}{|r' - r|} dr'^3 \quad (11)$$
$$= d(r) * \chi(r)$$

where $\delta(r)$ is the local magnetic field distribution, $\chi(r)$ is the magnetic susceptibility distribution within a biological body, $\alpha$ is the angle formed between the direction of the vector (r'−r) and the direction of the static magnetic field, d(r) is the point dipole magnetic field.

Namely, as shown in eq. (11), the local magnetic field distribution d(r) can be represented as a convolution integration of the magnetic susceptibility c(r) and the point dipole magnetic field d(r). Thus, by applying a Fourier transformation on both side of eq. (11), eq. (11) can be transformed into eq. (12).

[eq. 12]

$$\Delta(k) = \left(\frac{1}{3} - \frac{k_z^2}{k_x^2 + k_y^2 + k_z^2}\right) \cdot X(k) \quad (12)$$
$$= D(k) \cdot X(k)$$

where k=($k_x$, $k_y$, $k_z$) represents a position vector in a k-space, $\Delta(k)$ represents Fourier components of the local magnetic field distribution $\delta(r)$, D(k) represents Fourier components of the point dipole magnetic field d(r), X(k) represents Fourier components of a magnetic susceptibility distribution $\chi(r)$ As shown in eq. (12), the Fourier components X(k) of the magnetic susceptibility distribution $\chi(r)$ within a biological body can be calculated through dividing the Fourier components $\Delta(k)$ of the local magnetic field distribution $\delta(r)$ by the Fourier components D(k) of the point dipole magnetic field d(r).

However, since the inverse of D(k) diverges in the region close to D(k)=0, it is not possible to calculate $\chi(k)$ directly. The region close to D(k)=0 is called as "Magic Angle Region", which becomes an inverted bicone having a vertex angle of ca. twice 54.7 degree against the static magnetic field direction.

Because the QSM method is reduced to an ill-conditioned inverse problem due to the presence of the magic angle region, several solution methods are proposed for solving the ill-conditioned inverse problem. As representative solution methods for solving the ill-conditioned inverse problem, for example, under a constraint condition based on the relation between the magnetic field and the magnetic susceptibility, a method in which smoothing of the magnetic susceptibility distribution calculated from the magnetic field distribution is repeated, the TKD (Truncated-based K-space Division)-method in which the magnetic susceptibility distribution is calculated by operation of the magnetic field distribution and the point dipole magnetic field in k-space, the Iterative SWIM (Susceptibility Weighted Imaging and Mapping)-method in which the magnetic susceptibility distribution calculated by the TKD-method and the magnetic susceptibility distribution for a extracted fine structure by use of threshold value processing are combined by iterative operation, and the MEDI (Morphology enabled dipole inversion)-method by use of the regularized least square method can be considered. It should be noted that the customized distribution calculation unit 340 may utilize any of the mentioned methods.

<<Calculation Method for Magnetic Susceptibility Enhanced Image by SWI-Method>>

Next, the calculation method for a magnetic susceptibility enhanced image by use of the SWI-method is explained. The SWI-method generates a magnetic susceptibility enhancing mask for enhancing the magnetic susceptibility using the local phase distribution $P_{local}$ and calculates a magnetic susceptibility enhanced image through multiplying a measured intensity image (absolute-value image) by the magnetic susceptibility enhancing mask.

The customized distribution calculation unit 340 generates a predefined magnetic susceptibility enhancing mask and performs multiplication by this magnetic susceptibility enhancing mask for predetermined number of times. Subsequently, the customized distribution calculation unit 340 multiplies an absolute-value image with any echo time by this magnetic susceptibility enhancing mask, and thereby calculates a magnetic susceptibility enhanced image. Based on this image, the operator can determine whether the magnetic susceptibility is higher or lower. It should be noted that the customized distribution calculation unit 340 can calculate the magnetic susceptibility enhanced image by use of various methods, and therefore the use is not limited to the SWI-method.

[Image Display: S1005]

In step S1005, the computer 109 does an image display processing.

The computer 109 displays the quantitative magnetic susceptibility distribution or the magnetic susceptibility enhanced image, which are calculated in step S1004, on a display screen of the display unit 110. Further, the computer 109 can also store various data calculated in step S1004 in the external storage device 111 or in the auxiliary storage device and can also display the quantitative magnetic susceptibility distribution or the magnetic susceptibility enhanced image on a desired display device.

Here, in reference to FIG. 8, an example of the image displayed on the display unit 110 of the MRI-apparatus 100 is explained.

FIG. 8(*a*) is an image after applying the calculation processing by the computer 109 related to the present embodiment (a magnetic susceptibility enhanced image), and FIG. 8(*b*) is an enlarged view of an area 801 of FIG. 8(*a*). FIG. 8(*c*) is an image after applying the calculation processing by a conventional computer (a magnetic susceptibility enhanced image), and FIG. 8(*d*) is an enlarged view of an area 802 of FIG. 8(*c*).

When the images of FIGS. 8(*a*), 8(*b*) and the images of FIGS. 8(*c*), 8(*d*) are compared, in the images of FIGS. 8(*a*) and 8(*b*), the brain surface area is clearly imaged, whereas, in the images of FIGS. 8(*c*) and 8(*b*), it can be seen that the brain surface area is not calculated. Namely, it is apparent that the computer 109 related to the present embodiment can calculate more information of the area surrounded with the thick line compared with a conventional computer.

Therefore, when the operator makes a diagnosis of a structure or a composition of biological tissue in total brain, he can make a more appropriate diagnosis by using the images of FIGS. 8(*a*) and 8(*b*) rather than by using the images of FIGS. 8(*c*) and 8(*d*). Further, when the operator makes a diagnosis of a lesion occurred on the brain surface such as subarachnoid hemorrhage, brain infarction, etc., he can make an accurate diagnosis by using the images of FIGS. 8(*a*) and 8(*b*). Namely, applying a predetermined calculation processing by the computer 109 related to the present embodiment, the operator can obtain a highly reliable image of the brain surface area.

As above, by carrying out above explained respective processing, the calculation process executed by the computer 109 related to the present embodiment is terminated. It should be noted that the flow diagrams shown in the above explained FIGS. 4 and 6 are merely examples, it is needless to say that it is possible to omit a portion or to add another process.

According to the MRI-apparatus related to the present embodiment, the computer 109 extracts, for example, a brain area from a complex image, divides the total phase distribution into the brain surface area and to the area of brain inside, calculates the background phase distribution in the brain surface area, combines the total phase distribution and the background phase distribution, and thereby calculates the local phase distribution of total brain. Due to this, an MRI-apparatus for calculating the local phase distribution of total brain including the brain surface area with high accuracy can be realized.

Further, according to the MRI-apparatus related to the present embodiment, a quantitative magnetic susceptibility distribution and a magnetic susceptibility enhanced image can be calculated by use of the highly accurate local phase distribution. Due to this, since the operator can obtain an image having a widened clear image area, the reliability of a diagnosis can be improved.

REFERENCE SIGNS LIST

100, 120, 130 magnetic imaging apparatus
101 subject
102 static magnetic field generating magnet
103 gradient magnetic field application unit
105 transmission unit
106 reception unit
109 computer
110 display unit
331 subject tissue extracting unit
332 phase distribution calculation unit
333 phase wrapping correction unit
334 area dividing unit
335 background phase distribution calculation unit
336 total areal local phase distribution calculation unit (local phase distribution calculation unit)

The invention claimed is:

1. A magnetic resonance imaging apparatus, comprising:
a static magnetic field generation magnet configured to generate a static magnetic field in a space where a subject is arranged;
a transmission unit configured to transmit a high frequency magnetic field to the subject;
a reception unit configured to receive a nuclear magnetic resonance signal generated in the subject through transmission of the high frequency magnetic field thereto;
a gradient magnetic field application unit configured to apply a gradient magnetic field which adds positional information to the nuclear magnetic resonance signal;
a computer configured to control the transmission unit, the reception unit, and the gradient magnetic field application unit, and configured to process the nuclear magnetic resonance signal; and,
a display unit configured to display an image processed by the computer;
wherein
the computer comprises:
a subject tissue extracting unit configured to compute a subject tissue extraction image for a extracted tissue of the subject tissue, from a complex image composed of the nuclear magnetic resonance signals,
a phase distribution calculation unit configured to calculate the phase distribution from the complex image,
a phase wrapping correction unit configured to correct a phase wrapping of the phase distribution,
an area dividing unit configured to divide the phase distribution after correction into a predetermined area and an area other than the predetermined area of the subject tissue, based on the subject tissue extraction image, a background phase distribution calculation unit configured to calculate a background phase distribution of the predetermined area, and a local phase distribution calculation unit configured to calculate a local phase distribution in the predetermined area of the subject tissue by combination of the phase distribution after correction and the background phase distribution.

2. The magnetic resonance imaging apparatus according to claim 1, wherein the local phase distribution calculation unit calculates the local phase distribution, based on a condition that a pixel-value in any pixel is approximately equivalent to an averaged pixel-value of pixels within a sphere having a predetermined radius with a center at the any pixel.

3. The magnetic resonance imaging apparatus according to claim 2, wherein the local phase distribution calculation unit calculates the local phase distribution, based on a condition to minimize a regularization term of the local phase distribution.

4. The magnetic resonance imaging apparatus according to claim 1, wherein the computer calculates a local magnetic field distribution using the local phase distribution and calculates a magnetic susceptibility distribution using the local magnetic field distribution and a relation between magnetic field and magnetic susceptibility.

5. The magnetic resonance imaging apparatus according to claim 4, wherein the computer generates a magnetic susceptibility enhancing mask for enhancing the magnetic susceptibility using the local phase distribution and calculates a magnetic susceptibility enhanced image by multiplying an absolute-value components image of the complex image by the magnetic susceptibility enhancing mask.

6. The magnetic resonance imaging apparatus according to claim 1, wherein the area dividing unit divides the phase distribution after correction into a brain surface area and to an area of brain inside.

* * * * *